US008603545B2

(12) United States Patent
Moser et al.

(10) Patent No.: US 8,603,545 B2
(45) Date of Patent: Dec. 10, 2013

(54) **COSMETIC AND PHARMACEUTICAL USES OF AN EXTRACT OF A PLANT BELONGING TO THE GENUS *BUCHHOLZIA***

(75) Inventors: Philippe Moser, Essey-les-Nancy (FR); Louis Danoux, Saulxures les Nancy (FR); Gilles Pauly, Nancy (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 1182 days.

(21) Appl. No.: 10/593,850

(22) PCT Filed: Mar. 15, 2005

(86) PCT No.: PCT/EP2005/002729
§ 371 (c)(1),
(2), (4) Date: Sep. 22, 2006

(87) PCT Pub. No.: WO2005/089705
PCT Pub. Date: Sep. 29, 2005

(65) Prior Publication Data
US 2007/0178059 A1    Aug. 2, 2007

(30) Foreign Application Priority Data
Mar. 24, 2004    (EP) ..................................... 04290788

(51) Int. Cl.
*A61K 36/00*    (2006.01)
(52) U.S. Cl.
USPC ........................................................ 424/725
(58) Field of Classification Search
None
See application file for complete search history.

(56) References Cited

U.S. PATENT DOCUMENTS 4,343,798 A * 8/1982 Fawzi ........................... 514/179

FOREIGN PATENT DOCUMENTS

| JP | 362161724 A | * | 7/1987 |
| JP | 411322630 A | * | 11/1999 |
| JP | 02000159632 A | * | 6/2000 |

OTHER PUBLICATIONS

Ajaiyeoba (Antimicrobial and cytotoxicity evaluation of *Buchholzia coriacea* stem bark, Fitoterapia 74 (2003) pp. 706-709).*
Burkill (The useful plant of West Africa (*Buchholzia coriacea*), vol. 1, 1985).*
Ajaiyeoba, et al., "Antimicrobial and Cytotoxicity Evaluation of *Buchholzia coriacea* Stem Bark", Fitoterapia, vol. 74, (2003), pp. 706-709 (XP-002330674).
Ajaiyeoba, "Phytochemical and Antimicrobial Studies of *Gynandropsis gynandra* and *Buchholzia coriaceae* Extracts", African Journal of Biomedical Research, vol. 3, No. 3, (2000), pp. 161-165 (XP-002330675).
Delaveau, et al., "Alcaloïdes Chez Les Capparidaceae", Phytochemistry, vol. 12, (1973), pp. 2893-2895.
Koudogbo, et al, "Sur une Capparidacée africaine, le *Buchholzia coriacea* Engler", Annales Pharmaceutiques Francaises, vol. 30, No. 2, (1972), pp. 93-98.
Ajaiyeoba, et al., "In vitro Anthelmintic Properties of *Buchholzia coriaceae* and *Gynandropsis gynandra* Extracts", Pharmaceutical Biology, vol. 39, No. 3, (2001), pp. 217-220.
Vivien, et al., "Fruitiers Sauvages du Cameroun", Fruits, vol. 43, No. 9, (1988), pp. 507-513.
Wickens, "Edible Nuts", Non-Wood Forest Products, No. 5, FAO Editor, (1995), p. 113.
Bradford, "A Rapid and Sensitive Method for the Quantitation of Microgram Quantities of Protein Utilizing the Principle of Protein-Dye Binding", Analytical Biochemistry, vol. 72, (1976), pp. 248-254.
Hissin et al., "A Fluorometic Method for Determination of Oxidized and Reduced Glutathione in Tissues", Analytical Biochemistry, vol. 74, (1976), pp. 214-226.
Desaulniers, et al., "Optimization of an MCF7-E3 Cell Proliferation Assay and Effects of Environmental Pollutants and Industrial Chemicals", Toxicology In Vitro, vol. 12, (1998), pp. 409-422.
Vasseur, et al., "Appréciation De La Cytotoxicité Par La Mesure De L'A.T.P.", Journal Francais d'Hydrologie, vol. 9, (1978), pp. 149-156.
Ajaiyeoba, E. O., "Phytochemical and Antimicrobial Studies of *Gynandropsis gynandra* and *Buchholzia coriaceae* Extracts", *Afr. J. Biomed. Res.*, vol. 3 2000, 161-165.

* cited by examiner

*Primary Examiner* — Terry A McKelvey
*Assistant Examiner* — Randall Winston
(74) *Attorney, Agent, or Firm* — Servilla Whitney LLC

(57) ABSTRACT

A cosmetic or dermopharmaceutical composition including an extract of a plant belonging to the genus *Buchholzia* and at least one auxiliary and/or additive is provided. A method for the cosmetic treatment of the skin or scalp and a method for the treatment of skin inflammation includes administering to a patient in need thereof a composition including an effective amount of a plant extract from a plant belonging to the genus *Buchholzia*.

4 Claims, No Drawings

COSMETIC AND PHARMACEUTICAL USES OF AN EXTRACT OF A PLANT BELONGING TO THE GENUS *BUCHHOLZIA*

The present invention is concerned with a composition comprising an extract of a plant belonging to the genus *Buchholzia* and auxiliaries and/or additives, which are common for cosmetic purposes. Said composition and said extract can be used for cosmetic purposes. Furthermore said extract can be used for pharmaceutical purposes.

The genus *Buchholzia* belongs to the botanical family Capparidaceae. The plant *Buchholzia coriacea* Engler is one plant that belongs to the genus *Buchholzia*. Synonyms of the name *Buchholzia coriacea* Engler are *Buchholzia coriacea*, *Buchholzia coriaceae* and *Buchholzia coreacea*.

*Buchholzia tholloniana* and *Buchholzia macrophylla* are other species which belong to the genus *Buchholzia*.

The plant *Buchholzia coriacea* is a shrub or medium-sized tree, evergreen, with a dense crown, large glossy leathery leaves arranged spirally and clustered at the ends of the branches, and conspicuous cream-white flowers in racemes at the end of the branches. The bark of the plant *Buchholzia coriacea* is smooth, blackish-brown or dark-green. Slashes are deep red turning dark brown.

The leaves of the plant *Buchholzia coriacea* can be described as follows: large, obovate, oblanceolate to elliptic, shortly acuminate or acute at apex, cuneate at base, 15-30× 5-11 cm, thinly coriaceous, glabrous, midrib very prominent below, about 10 lateral nerves, each running directly into the one above and forming distinct loops close to the margin, prominent below, stalk 10-15 cm long, swollen for about 1 cm at both ends, pale green.

The flowers of the plant *Buchholzia coriacea* can be described as follows: in simple or lightly-branched lax racemes among the leaves at the ends of the shoots, up to 24 cm long, individual flowers with a stalk less than 1.3 cm. 4 small rounded sepals bent right back exposing the thick saucer-shaped purplish receptacle, without petals, 40 to 45 stamens with cream-yellow filaments and small purplish-black anthers and a narrow elongated ovary projecting beyond the stamens at the end of a thin stalk.

The fruits of the plant *Buchholzia coriacea* can be described as follows: large, long-stalked, ellipsoid, resembling avocado pears, 12×5-8 cm, endocarp up to 1.3 cm thick and woody, yellowish when ripe, flesh yellow, edible, containing a few large blackish seeds, about 2.5 cm long.

The plant *Buchholzia coriacea* is a tree of the lowland rain forest in the region Guinea to Cameroon, and in Gabon. In Gabon the plant *Buchholzia coriacea* is sometimes cultivated as a medicinal and fetish plant.

Vernacular names of the plant *Buchholzia coriacea* are Cola pimento, elephant cola, oignon de Gorille.

Plants that belong to the botanical family Capparidaceae have been used in traditional ethnomedicine for several years and several genera of plants have been documented for the treatment of various ailments.

Plants that belong to the botanical family Capparidaceae have been used for the treatment of syphilis, dressing of wounds, chronic ulcers and for the treatment of snake bites. Certain plants of the family Capparidaceae have been used for the treatment of gonorrhoea, convulsion in children, as aphrodisiacs and as anthelmintics.

In the Ivory coast the twig bark decoction of the plant *Buchholzia coriacea* is used for the treatment of rheumatism and kidney pain, it is also used for the treatment infections of the eye (bark gruel poured into the flat of the hand and inhaled) and for the treatment of pain in the back (fruit pulp massaged in). For the treatment of earache, seeds are pounded in a little bit of water and the resulting liquid is dropped into the ear. The Ebrié tribes bathe smallpox victims with the bark decoction of the plant *Buchholzia coriacea*. The sharp-tasting seed arils of the plant *Buchholzia coriacea* are chewed like cola. In Sierra Leone a paste is made from leaves of the plant *Buchholzia coriacea*, fruit and white clay, which is rubbed on the body for the treatment of fever. In Nigeria, the fruit of the plant *Buchholzia coriacea* is used as an anthelmintic. In Liberia, the seeds of the plant *Buchholzia coriacea* are used internally against worms and pain, externally against skin diseases. In Cameroon, a medicine is made from the fruit of the plant *Buchholzia coriacea* for the treatment of coughs. Young leaves of the plant *Buchholzia coriacea* are used in a gruel poultice for ulcers and boils. In Gabon pounded bark of the plant *Buchholzia coriacea* is used as a lotion against scabies, the fruit of the plant *Buchholzia coriacea* as an anthelmintic. In former times young warriors were given fresh roots of the plant *Buchholzia coriacea* to stimulate them before battle.

Little is known about the chemical composition of the plant *Buchholzia coriacea*. The plant family Capparidaceae is well known for the presence of glucosinolates and alcaloids.

According to Delaveau et al. (Delaveau P., Koudogbo B, Pousset J L.: Alcaloïdes chez les Capparidaceae, Phytochemistry, 1973, volume 12, pages 2893 to 2895), leaf samples of the plant *Buchholzia coriacea* from the Ivory Coast do not contain the alkaloid L-stachydrine and the hydroxides of tetramethylammonium, whereas these substances are found in numerous members of the family Capparidaceae.

From the bark of stems of the plant *Buchholzia coriacea* Koudogbo et al. have extracted the pentacyclic triterpene lupeol and the sterols campesterol, stigmasterol and β-sitosterol as well as the aglycone of three anthocyans: pelargonidin (red-violet) cyanidin (red) and apigenidin (yellow). Three glucosinolates were found, one of them has been identified as glucocapparine, the characteristic compound of plants of the family Capparidaceae. Preliminary tests have also shown that leaves, trunk bark and roots of the plant *Buchholzia coriacea* contain tannins, proanthocyans and glycosinolates and seem to be devoided of quinones, flavonoids and alkaloids (Koudogbo B, Delaveau P., Adjanohoun. E.: Sur une Capparidacée africaine, le *Buchholzia coriacea* Engler, Annales Pharmaceutiques Francaises, 1972, volume 30, pages 93 to 98).

Methanol extracts of leaves and stems of the plant *Buchholzia coriaceae* showed anthelmintic activity in vitro (Ajaiyeoba E O, Onocha P. A, Olarenwaju O T.: In vitro anthelmintic properties of *Buchholzia coriaceae* and *Gynandropsis gynandra* extracts, Pharmaceutical Biology, 2001, volume 39, pages 217 to 220).

The publications "VIVIEN J, FAURE J J, Fruitiers sauvages du Cameroun, Fruits, volume 43, 1988, pages 507 to 513" and "G. E. WICKENS, Non-wood Forest products, no 5-Edible nuts, FAO editor, 1995 page 113" disclose that the seeds or kernels of the plant *Buchholzia coriaceae* are edible and that they have a spicy taste and that they can be used as a condiment (spice).

The ground seeds or kernels of the plant *Buchholzia coriaceae* are a component of a traditional and valued aphrodisiac or stimulant that is sold on local markets in Africa (Cameroon). The African plant *Buchholzia coriaceae* is used as stimulant, tonic, aphrodisiac.

The subject of the present invention is based on the discovery that the extracts of a plant belonging to the genus *Buchholzia*, especially the seeds/kernels of the plant *Buchholzia coriacea*, have properties which allow their use as an active ingredient in cosmetics, especially in dermatological compositions intended to fight effects linked to the ageing of human skin. Furthermore these extracts are useful for pharmaceutical applications that are related to the treatment of diseases of the human skin.

One subject of the present invention is a composition comprising an extract of a plant belonging to the genus *Buchholzia* and auxiliaries and/or additives, which are common for cosmetic purposes. This composition is called the composition according to the present invention.

In one embodiment of the present invention the auxiliaries and/or additives which are common for cosmetic purposes are selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

One embodiment of the present invention is the composition according to the present invention, wherein the concentration of the extract in the composition is 0.001 weight-% to 25 weight-%. The amount in weight-% is calculated as the weight of the dry extract in relation to the weight of the composition.

One embodiment of the present invention is the composition according to the present invention, whereby the extract is an extract of the plant *Buchholzia coriazea* or of its parts.

One embodiment of the present invention is the composition according to the present invention, whereby the extract is an extract of the fruits, preferably of the hulled or dehulled seeds, of the plant *Buchholzia coriazea*.

One embodiment of the present invention is the composition according to the present invention, whereby the extract is obtainable by
a) extracting the plant belonging to the genus *Buchholzia* or parts of this plant with a solvent selected from the group consisting of water, an alcohol and mixtures thereof so that a solution of the extract in the solvent is obtained, and
b) removing the solvent from this solution, so that the extract is obtained.

In one embodiment of the present invention said solvent is either water or 70 vol-% ethanol in water.

Polar solvents or mixtures of different polar solvents, e. g. water or mixtures of water and alcohols (preferably alcohols with 1 to 6 C-atoms, e. g. methanol, ethanol or isopropanol) are preferred solvents for the preparation of the extract according to the present invention.

Polyols with 2 to 6 C-atoms, e. g. propylene glycol or glycerol or mixtures thereof, can also be used as alcohols in the solvent mixture described above.

Apolar or less polar solvents are also suitable (e. g. supercritical carbon dioxide may be used).

Microwaves or ultrasound may be used to support the extraction.

Another subject of the present invention is the use of an extract of a plant belonging to the genus *Buchholzia* or of the composition according to the present invention for the cosmetic treatment of the human body (preferably of the human skin or scalp). This use is called the use according to the present invention.

Preferred embodiments of this use are given if the plant is a plant as specified above (or if the parts of the plant as specified above are used). Furthermore preferred embodiments of this use are given if the extract is obtained as specified above.

Further embodiments of the use according to the present invention are uses according to the present invention, whereby the cosmetic treatment comprises the stimulation of the growth and/or metabolism of human fibroblasts or the stimulation of synthesis of proteoglycans such as lumican and/or syndecan or an anti-aging and/or anti-wrinkle effect or a revitalizing or rejuvenating effect on stressed or tired skin or the promotion of the repair of aged and/or photo-aged skin or the promotion of hair growth or the delay of hair loss or an appeasing and anti-irritation effect, particularly against oxidative stress and pollutants or a protease inhibition effect or an antioxidant effect or the protection against UV-radiation or the protection against IR-radiation or a decreasing effect on skin inflammation.

A further embodiment of the use according to the present invention is a use according to the present invention, whereby the cosmetic treatment comprises the treatment of sensitive skin, particularly of dry skin.

A further embodiment of the use according to the present invention is a use according to the present invention, whereby the cosmetic treatment comprises an inhibiting effect on the synthesis of melanin or a skin whitening effect or a decreasing effect on skin pigmentation, or whereby the cosmetic treatment comprises the treatment of aged spots.

Another subject of the present invention is the use of an extract of a plant belonging to the genus *Buchholzia* for the production of a cosmetic composition, preferably for the production of a composition according to any of claims 1 to 4.

Another subject of the present invention is the use of an extract of a plant belonging to the genus *Buchholzia* for the manufacture of a medicament for the treatment of skin inflammation or for the treatment of Rosacea. Rosacea is a disease characterized by an erythema coming from a permanent dilatation of dermis vasculature which occur most frequently in women aged 20 to 50 years. Repeated facial flushing, due to a vascular hyperactivity, are responsible of Rosacea to taking hold.

Preferred embodiments of the subjects of the present invention as defined in the two preceding paragraphs are given if the extract or the plant is defined more specifically (analogous to what has been defined for the composition and the use according to the present invention).

The numerous advantages of the subjects of the present invention are reflected, inter alia, in the preceding paragraphs (e. g. stimulation of the growth of human fibroblasts) and in the examples.

The auxiliaries and additives which are common for cosmetic purposes can be selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In one embodiment of the present invention the auxiliaries and additives which are common for cosmetic purposes are selected from the group consisting of surfactants, emulsifiers, fats, waxes, stabilizers, deodorants, antiperspirants, antidandruff agents and perfume oils.

The total content of auxiliaries and additives may be 1 to 50% by weight, preferably 5 to 40% by weight, based on the cosmetic and/or pharmaceutical preparations. The preparations can be prepared by customary cold or hot processes; preference is given to using the phase-inversion temperature method.

For the purposes of the invention, cosmetic preparations can mean care agents. Care agents are understood as meaning care agents for skin and hair. These care agents include, inter alia, cleansing and restorative action for skin and hair.

Application can be topical or oral in the form of tablets, dragees, capsules, juices, solutions and granules.

The compositions and cosmetic preparations according to the invention can be used for the preparation of cosmetic and/or dermopharmaceutical preparations, e. g. hair shampoos, hair lotions, foam baths, shower baths, creams, gels, lotions, alcoholic and aqueous/alcoholic solutions, emulsions, wax/fat compositions, stick preparations, powders or ointments. Furthermore, the preparations for oral application according to the invention can also be incorporated into tablets, dragees, capsules, juices, solutions and granules.

Surfactants (or Surface-active substances) that may be present are anionic, non-ionic, cationic and/or amphoteric or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e. g. acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants contain polyglycol ether chains, these may have a conventional homologous distribution, but preferably have a narrowed homologous distribution. Typical examples of non-ionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the non-ionic surfactants contain polyglycol ether chains, these may have a conventional homologous distribution, but preferably have a narrowed homologous distribution. Typical examples of cationic surfactants are quaternary ammonium compounds, e. g. dimethyldistearyl-ammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium-betaines and sulfobetaines. Said surfactants are known compounds. With regard to structure and preparation of these substances, reference may be made to relevant review works.

Typical examples of particularly suitable mild, i.e. particularly skin-compatible surfactants are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Suitable oily bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxucarboxylic acids with linear or branched $C_6$-$C_{22}$-fatty alcohols, in particular dioctyl malates, esters of linear and/or branched fatty acids with polyhydric alcohols (for example propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonates (Cetiol® CC) Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, for example dicaprylyl ether (Cetiole® OE), ring-opening products of epoxidized fatty acid esters with polyols, silicone oils (cyclomethicones, silicon methicone types, inter alia) and/or aliphatic or naphthenic hydrocarbons, for example squalane, squalene or dialkylcyclohexanes.

Suitable emulsifiers are, for example, nonionogenic surfactants from at least one of the following groups:
  addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;
  alkyl and/or alkenyl oligoglycosides having 8 to 22 carbon atoms in the alk(en)yl radical and the ethoxylated analogs thereof;
  addition products of from 1 to 15 mol of ethylene oxide onto castor oil and/or hydrogenated castor oil;
  addition products of from 15 to 60 mol of ethylene oxide onto castor oil and/or hydrogenated castor oil;
  partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;
  partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen® grades (TR-1, TR-2) from Goodrich;

polyalkylene glycols and glycerol carbonate.

The addition products of ethylene oxide and/or of propylene oxide onto fatty alcohols, fatty acids, alkylphenols or onto castor oil are known, commercially available products. These are homologous mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known as refatting agents for cosmetic preparations.

Alkyl and/or alkenyl oligoglycosides, their preparation and their use are known from the prior art. They can be prepared by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value that is based on a homologous distribution customary for such technical-grade products.

Typical examples of suitable partial glycerides are hydroxy stearic acid monoglyceride, hydroxy stearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linoleic acid monoglyceride, linoleic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolane® GI 34), polyglyceryl-3 oleate, diisostearoyl polyglyceryl-3 diisostearate (Isolane® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds that carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name *Cocamidopropyl Betaine*. Likewise suitable emulsifiers are ampholytic surfactants. The term "ampholytic surfactants" means those surface-active compounds that, apart from a $C_{8/18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacylaminoethyl aminopropionate and $C_{12/18}$-acylsarcosine. Finally, cationic surfactants are also suitable emulsifiers, those of the ester quat type, preferably methyl-quaternized difatty acid triethanolamine ester salts, being particularly preferred.

Fats and waxes that can be used are described in the following text. Typical examples of fats are glycerides, i.e. solid or liquid vegetable or animal products which consist essentially of mixed glycerol esters of higher fatty acids, suitable waxes are inter alia natural waxes, for example candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. Lecithins are thus frequently also [lacuna] as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying agents and thickeners that can be used are described in the following text. Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopolse and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, for example ethoxylated fatty acid glycerides, esters of fatty acids with polyols for example pentaerythritol or trimethylolpropane, fatty alcohol ethoxylates having a narrowed homolog distribution or alkyl oligoglucosides, and electrolytes such as sodium chloride and ammonium chloride.

Superfatting agents which can be used are for example lanolin and lecithin, and poly-ethoxylated or acylated lanolin and lecithin derivatives, polyol fatty acid esters, monoglycerides and fatty acid alkanolamides, the latter also serving as foam stabilizers.

Stabilizers which can be used are metal salts of fatty acids, for example magnesium, aluminium and/or zinc stearate or ricinoleate.

Polymers that can be used are described in the following text. Suitable cationic polymers are, for example, cationic cellulose derivatives, for example a quaternized hydroxyethylcellulose obtainable under the name Polymer JR 400® from Amerchol, cationic starch, copolymers of diallylammonium salts and acryl amides, quaternized vinylpyrrolidone-vinylimidazole polymers, for example Luviquate (BASF), condensation products of polyglycols and amines, quaternized collagen polypeptides, for example lauryidimonium hydroxypropyl hydrolysed collagen (Lamequat® L/Grünau), quaternized wheat polypeptides, polyethyleneimine, cationic silicone polymers, for example amodimethicones, copolymers of adipic acid and dimethylaminohydroxypropyl diethylenetriamine (Cartaretins®/Sandoz), copolymers of acrylic acid with dimethyl diallylammonium chloride (Merquat® 550/Chemviron), polyaminopolyamides and cross linked water-soluble polymers thereof, cationic chitin derivatives, for example quaternized chitosan, optionally in microcrystalline dispersion, condensation products from dihaloalkyls, for example dibromobutane with bisdialkylamines, for example bis-dimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

Deodorants and antimicrobial agents that can be used are described in the following text. Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, for example 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorohexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, for example n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise one or more of the following ingredients: astringent active ingredients, oil components, nonionic emulsifiers, coemulsifiers, bodying agents, auxiliaries, for example thickeners or complexing agents, and/or nonaqueous solvents, for example ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium penta-chlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be anti-inflammatory, skin-protective or perfumed ethereal oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, for example xanthan gum, hydroxyethylcellulose, polyvinylpyrrolidone or high molecular weight polyethylene oxides.

Film formers that can be used are described in the following text. Customary film formers are, for example, chitosan, microcrystalline chitosan, quaternized chitosan, poly-vinylpyrrolidone, vinylpyrrolidone-vinyl acetate copolymers, polymers of the acrylic acid series, quaternary cellulose derivatives, collagen, hyaluronic acid and salts thereof, and similar compounds.

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicyclic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

The swelling agents for aqueous phases may be montmorillonites, clay mineral substances, Pemulen, and alkyl-modified Carbopol grades (Goodrich).

Suitable insect repellents are N,N-diethyl-m-toluamide, 1,2-pentanediol or ethyl butylacetylaminopropionate.

To improve the flow behavior, hydrotropes, for example ethanol, isopropyl alcohol, or polyols, can be used. Polyols which are suitable here preferably have 2 to 15 carbon atoms and at least two hydroxyl groups. The polyols can also contain further functional groups, in particular amino groups, or be modified with nitrogen. Typical examples are:

glycerol;

alkylene glycols, for example, ethylene glycol, diethylene glycol, propylene glycol, butylene glycol, hexylene glycol, and polyethylene glycols with an average molecular weight of from 100 to 1 000 daltons;

technical-grade oligoglycerol mixtures with a degree of self-condensation of from 1.5 to 10, for example, technical-grade diglycerol mixtures with a diglycerol content of from 40 to 50% by weight;
methylol compounds, such as trimethylolethane, trimethylolpropane, trimethylol-butane, pentaerythritol and dipentaerythritol;
lower alkyl glucosides, in particular those with 1 to 8 carbon atoms in the alkyl radical, for example methyl and butyl glucoside;
sugar alcohols with 5 to 12 carbon atoms, for example sorbitol or mannitol,
sugars with 5 to 12 carbon atoms, for example glucose or sucrose;
amino sugars, for example glucamine;
dialcohol amines, such as diethanolamine or 2-amino-1,3-propanediol.

Suitable preservatives are, for example, phenoxyethanol, formaldehyde solution, parabenes, pentanediol or sorbic acid, and the other classes of substance listed in Annex 6, Part A and B of the Cosmetics Directive.

Perfume oils which may be used are preferably mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Dyes which can be used are the substances which are approved and suitable for cosmetic purposes. These dyes are normally used in concentrations of from 0.001 to 0.1% by weight, based on the total mixture.

EXAMPLES

% (w/v) means "% weight by volume", 1% (w/v) means 1 g per 100 ml.

Example 1

Hot Water Extract 200 g of dry seeds of the plant *Buchholzia coriacea* were crushed in a blade crusher. Then they were introduced in a glass reactor containing 2 liters of distilled water (ratio raw material to solvent=1 to 10). Extraction was carried out under shaking for one hour at a temperature of 80 to 85° C. Then the mixture was cooled to room temperature (20° C.). The liquid and the solid fraction were separated by centrifugation at 5000 g for 15 min and subsequent filtration through depth filters (0.45 μm). The yellow extract was dried by spray-drying. The yield based on extracted seeds was 13.6%.

Example 2

Water Extract at Room Temperature 200 g of dry seeds of the plant *Buchholzia coriacea* were crushed in a blade crusher. Then they were introduced in a glass reactor containing 2 liters of distilled water (ratio raw material to solvent=1 to 10). Optionally, the suspension could be treated with ultrasonic to accelerate the extraction (conditions: time: 10 minutes, pulse: 5 seconds, time of latency between 2 pulsations: 9.9 seconds, amplitude: 100%). The suspension was extracted under shaking for one hour at room temperature (25° C.). The liquid and the solid fraction were separated by centrifugation at 5000 g for 15 minutes and subsequent filtration through depth filters (0.45 μm). The filtrate was yellow. The yellow extract was dried by freeze-drying or by spray-drying. The yield based on extracted seeds was 8.9 to 14.5% depending on the batch of raw material used.

Example 3

Maltodextrine Addition

Maltodextrine (50% by weight) was added to the solution of example 3 before spray-drying.

Example 4

Extraction with a Mixture of Ethanol and Water (70% by Volume Ethanol)

In a glass reactor 2 liters of ethanol in water (70%) and 200 g of crushed seeds of the plant *Buchholzia coriacea* were combined. Extraction was carried out under shaking for 1 hour under reflux. Then the mixture was cooled to room temperature. The liquid and the solid fraction were separated by filtration through depth filters (5 μm). the insoluble residue was rinsed with 200 ml of ethanol (70% in water). The two filtrates were added and filtered through a 0.45 μm-filter. Concentration of the resulting liquid was carried out under vacuum at 30° C. Then it was freeze-dried. The yield of extract was 7.4 to 8.1% relative to the crushed seeds depending on the batch of raw material used.

Example 5

Revitalizing and Regenerating Effect of the Extracts According to Examples 1 to 3

Aim and Principle of Example 5:

The purpose of these tests is to evaluate the revitalizing and regenerating activities of plant extracts on human fibroblasts cultured in vitro.

Method of Example 5:

The growth efficacy test was carried out on human fibroblasts to evaluate the regenerating and the growth factor like activities. The survival efficacy test was carried out on human fibroblasts to evaluate the regenerating and the revitalizing activities.

The cell number and the cell viability have been determined by recording the following parameters:

- Protein levels were evaluated according to Bradford's method (Bradford: A rapid and sensitive method for the quantification of microgram quantities of protein utilizing the principle of protein-dye binding, Analytical Biochemistry, volume 72, pages 248 to 254, 1976)
- Glutathione (GSH) is a peptide produced by the cells to protect them against oxidative stress or against certain pollutants like mercury or lead. The three amino acids involved into the reduced form of GSH are linked by specific cytoplasmic enzymes which use ATP (adenosine triphosphate). The GSH level was evaluated by the method of Hissin (Hissin P. J., Hilf R.: A fluorometric method for determination of oxidized and reduced glutathione in tissues, Analytical Biochemistry, 1976, volume 74, pages 214 to 226)
- The DNA levels were evaluated with a fluorescent probe (Hoechst 33258) (Desaulniers D., Leingartner K., Zacharewski T. and W. G. Foster W. G.: Optimisation of an MCF7-E3 cell proliferation assay and effects of environmental pollutants and industrial chemicals, 1998, Toxic In vitro, volume 12 number 4, pages 409 to 422)
- ATP (adenosine triphosphate) is a compound rich in energy and mainly produced from mitochondria. The cells need ATP for the activity of many enzymes which control the cytoskeleton, the ionic channels, the nutriment intake, and a lot of other biological processes (Vasseur P., Aerts C.: Appréciation de la cytotoxicité par la mesure de l'ATP, Journal Français Hydrologie, 1981, volume 9, pages 149 to 156).

The results were calculated referring to a standard range and in percent versus the control and finally expressed as the average of typically 2 or 3 assays, carried out in triplicate.

Results: Activity on the Growth of Human Fibroblasts Cultured In Vitro

| Product | Batch | Dose % (w/v) | Level of proteins |
|---|---|---|---|
| Control | | — | 100 |
| Extract according to example 1 | / | 0.1 | 120 |
| Extracts according to example 2 | A | 0.3 | 136 |
| | B | 0.1 | 129 |
| | C | 0.1 | 131 |
| Extract according to example 3 (50% by weight maltodextrine) | / | 0.03 | 123 |
| Extract according to example 4 | A | 0.1 | 148 |
| | B | 0.1 | 130 |
| | C | 0.1 | 121 |
| | D | 0.03 | 115 |

Results: Activity on the Metabolism of Human Fibroblasts Cultured In Vitro

| Product | Batch | Dose % (w/v) | ATP level | protein level | GSH/ protein level | DNA level |
|---|---|---|---|---|---|---|
| Control | | — | 100 | 100 | 100 | 100 |
| Foetal Calf Serum | | 1 | 153 | 148 | 103 | 125 |
| Extract according to example 1 | / | 0.1 | 103 | 116 | 122 | 117 |
| | | 0.3 | 154 | 125 | 147 | 131 |
| Extracts according to example 2 | A | 0.1 | 186 | 141 | 126 | 130 |
| | | 0.3 | 186 | 170 | 114 | 164 |
| | B | 0.03 | 126 | 129 | 123 | 109 |
| | | 0.1 | 138 | 124 | 144 | 117 |
| | | 0.3 | 156 | 133 | 202 | 123 |
| | C | 0.1 | 177 | 165 | 117 | 152 |
| | | 0.3 | 178 | 197 | 124 | 165 |
| | D | 0.1 | 122 | 123 | 151 | 106 |
| | | 0.3 | 111 | 115 | 142 | 93 |
| Extract according to example 3 (50% by weight maltodextrine) | / | 0.03 | 126 | 133 | 129 | 109 |
| | | 0.1 | 122 | 135 | 128 | 111 |
| Extracts according to example 4 | A | 0.03 | 101 | 109 | 100 | 100 |
| | | 0.1 | 122 | 120 | 111 | 118 |
| | | 0.3 | 173 | 150 | 146 | 155 |
| | B | 0.03 | 90 | 110 | 109 | 99 |
| | | 0.1 | 120 | 134 | 144 | 132 |
| | | 0.3 | 132 | 132 | 145 | 118 |
| | C | 0.1 | 136 | 136 | 162 | 128 |
| | | 0.3 | 161 | 162 | 184 | 146 |
| | D | 0.03 | 98 | 103 | 147 | 103 |
| | | 0.1 | 113 | 112 | 172 | 121 |
| | | 0.3 | 125 | 107 | 193 | 120 |

Conclusions from Example 5:

- The extracts have not shown any toxic effect on cultured human fibroblasts 0.25-0.3% (w/v).
- The extracts at 0.1% (w/v) have distinctly improved the growth and the metabolism of human fibroblasts cultured in vitro.
- Therefore the extracts have presented a good potential as anti-aging, rejuvenant and revitalizing active ingredient for cosmetic applications.

Example 6

Inhibition of UVA Effect on Human Fibroblasts

Aim of the experiment: Determination of the potential of the tested ingredient to reduce negative effects of UV-A radiation on the survival rate of human fibroblasts.

Protocol of the Experiment:

- Seeding of human fibroblasts in a growth medium
- Incubation for 3 days at 37° C., CO2=5% (atmosphere: 5% carbon dioxide in air)
- Exchange of the growth medium by a medium with a range of concentration of ingredients to be tested
- Incubation for 2 days at 37° C., CO2=5%
- Exchange of the medium with ingredients by a balanced salt solution and UV-A irradiation (20 J/cm$^2$)
- Recording of released MDA levels by spectro-fluorimetry. (MDA (malonaldialdehyde) is a product of oxidative degradation of lipids from cell membranes)
- Recording of intracellular proteins by Bradford's method Results in % against control (average of 2 assays in triplicate):

| | Dose (% w/v) | Rate of released MDA | Intracellular proteins |
|---|---|---|---|
| Control | 0 | 0 | 100 |
| UV-A 20 J/cm2 | 0 | 100 | 99 |
| Vitamin E + UV-A | 0.0003 | 25 | 103 |
| Extract according to example 2 (batch E) + UV-A | 0.1 | 61 | 118 |
| | 0.3 | 45 | 153 |

UV-A irradiation has induced a strong release of MDA in human fibroblasts. Vitamin E has strongly decreased the rate of released MDA from UV-A irradiated fibroblasts. *Buchholzia* extract has shown a good potential to protect human fibroblasts from UVA toxicity.

Example 7

Inhibition of UVB Effect on Human Keratinocytes

Aim of the experiment: Determination of the potential of the tested ingredient to reduce negative effects of UV-B radiation on the survival rate of human keratinocytes.

It is well known that UV-B radiation induces a cutaneous inflammation by stimulation of enzymes such as phospholipase A2 (PLA2). This enzyme catalyses the release of arachidonic acid which is a precursor of mediators of inflammation like the prostaglandin PGE2. Moreover this membrane stress results in the release of a cytoplasmic enzyme: lactate dehydrogenase (LDH).

Protocol of the Experiment:
  Seeding of human keratinocytes in a growth medium
  Incubation for 3 days at 37° C., CO2=5% (atmosphere: 5% carbon dioxide in air)
  Exchange of the growth medium by balanced salt solution with a range of concentration of ingredients to be tested
  Irradiation of keratinocytes by UV-B: 30 mJ/cm$^2$
  Incubation for 1 day at 37° C., CO2=5%
  Recording of cell number by DNA measurement with a fluorescent probe
  Recording of the level of released LDH (by an enzymatic reaction) and released PGE2 (by ELISA method)

Results in % against control (average of 2 assays in triplicate):

| | Dose (% w/v) | Cell number | Level of released LDH | Level of released PGE2 |
|---|---|---|---|---|
| Control | 0 | 100 | 0 | 0 |
| UV-B 30 mJ/cm2 | 0 | 15 | 100 | 100 |
| Aspirin ® + UV-B | 0.03 | 59 | 8 | 0 |
| Extract according to example 2 (batch E) + UV-B | 0.1 | 24 | 53 | 45 |
| | 0.3 | 27 | 36 | 26 |

UV-B irradiation has induced a strong increase of the level of released LDH and PGE2 and a decrease of around 85% of the cell number. Aspirin has strongly decreased the level of released LDH and PGE2 and strongly increased the level of cell number from UV-B irradiated keratinocytes.

*Buchholzia* extract has shown a good potential to protect human keratinocytes from UV-B effects.

Example 8

Inhibition of Melanin Synthesis

Aim of the experiment: to evaluate the potential of compounds to lower the melanin synthesis; the compounds have been tested on a cell culture of melanocytes called B16.

Protocol of Efficacy Test on B16 Melanocytes:
  Seeding of melanocytes in growth medium
  Incubation for 3 days at 37° C., CO2=5% (atmosphere: 5% carbon dioxide in air)
  Exchange of the growth medium by a medium with a range of concentration of ingredients to be tested
  Incubation for 3 days at 37° C., CO2=5% (atmosphere: 5% carbon dioxide in air)
  Recording of Cellular levels of protein by Bradford's method
  Recording of melanin by a spectrophotometric method (OD at 475 nm)

Results in % against control (average of 2 assays in triplicate):

| | Dose (% w/v) | Rate of cellular proteins | Rate of melanin |
|---|---|---|---|
| Control | 0 | 100 | 100 |
| kojic acid | 0.03 | 117 | 34 |
| Extract according to example 2 (batch E) | 0.03 | 100 | 86 |
| | 0.1 | 109 | 61 |

Kojic acid has strongly decreased the rate of released melanin from treated B16 melanocytes. *Buchholzia* extract has shown a distinct inhibition of melanin synthesis.

What is claimed is:

1. A method of reducing melanin pigmentation of age spots in skin of a subject, the method comprising topically applying to the age spots a composition comprising: a seed extract of *Buchholzia coriacea* in an amount effective to reduce pigmentation of the age spots, wherein said seed extract is obtained by extracting seeds of the *Buchholzia coriacea* plant with a polar solvent.

2. The method of claim 1, wherein the seed extract has a concentration of 0.001 weight-% to 25 weight-% based on the composition.

3. The method of claim 1, wherein the composition further comprises at least one auxiliary and/or additive.

4. The method of claim 3 wherein the auxiliary and/or additive is selected from the group consisting of oil bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils, dyes, and mixtures thereof.

* * * * *